(12) United States Patent
Gilbert et al.

(10) Patent No.: US 10,392,594 B2
(45) Date of Patent: Aug. 27, 2019

(54) NANOCOMPOSITE SCAFFOLD FOR THE IN VITRO ISOLATION OF CELLS

(71) Applicant: Rensselaer Polytechnic Institute, Troy, NY (US)

(72) Inventors: Ryan James Gilbert, Troy, NY (US); Elizabeth Hager Cothren, Frederick, MD (US); Gregory Patrick Desmond, Marshfield, MA (US); Marc Andrew Burnette, Menifee, CA (US); Erica Victoria Hoey, Hollis Hills, NY (US); Stephanie Christine Krom, Troy, NY (US); Clarissa May Herman, Troy, NY (US)

(73) Assignee: Renssealer Polytechnic Institute, Troy, NY (US)

( * ) Notice: Subject to any disclaimer, the term of this patent is extended or adjusted under 35 U.S.C. 154(b) by 0 days.

(21) Appl. No.: 15/512,426

(22) PCT Filed: Sep. 28, 2015

(86) PCT No.: PCT/US2015/052639
§ 371 (c)(1),
(2) Date: Mar. 17, 2017

(87) PCT Pub. No.: WO2016/049627
PCT Pub. Date: Mar. 31, 2016

(65) Prior Publication Data
US 2017/0283759 A1    Oct. 5, 2017

Related U.S. Application Data

(60) Provisional application No. 62/056,013, filed on Sep. 26, 2014.

(51) Int. Cl.
| | |
|---|---|
| C12M 1/12 | (2006.01) |
| G01N 33/50 | (2006.01) |
| C12M 1/32 | (2006.01) |
| C12Q 1/02 | (2006.01) |
| C12M 3/00 | (2006.01) |

(Continued)

(52) U.S. Cl.
CPC ............. *C12M 25/14* (2013.01); *C07K 14/78* (2013.01); *C12M 21/08* (2013.01); *C12M 23/12* (2013.01);

(Continued)

(58) Field of Classification Search
None
See application file for complete search history.

(56) References Cited

U.S. PATENT DOCUMENTS

2012/0171257 A1    7/2012    Inanç et al.
2013/0266943 A1    10/2013    Powell

FOREIGN PATENT DOCUMENTS

WO    2012019049    2/2012
WO    WO-2013168979 A1    11/2013

OTHER PUBLICATIONS

Coutts, Amanda S; Adhesion Protein Protocols, 3rd Ed., Humana Press, 2013 (Year: 2013).*

(Continued)

*Primary Examiner* — David W Berke-Schlessel
(74) *Attorney, Agent, or Firm* — Murtha Cullina LLP

(57) ABSTRACT

The present invention is directed to devices, methods and kits for cell-specific sorting of cells from a mixed population, e.g., from a tumor sample. Aspects of the invention combine aligned, electrospun microfibers with drug- or protein-releasing nanospheres to isolate cancer cells from tumor biopsies.

14 Claims, 5 Drawing Sheets

(51) Int. Cl.
  C07K 14/78 (2006.01)
  C12M 1/00 (2006.01)
  C12N 5/00 (2006.01)
(52) U.S. Cl.
  CPC .......... C12M 25/02 (2013.01); C12M 47/04 (2013.01); C12Q 1/02 (2013.01); G01N 33/5088 (2013.01); *C12N 5/00* (2013.01); *C12N 2531/00* (2013.01)

(56) References Cited

OTHER PUBLICATIONS

Sundararaghavin, Harini G; et al; "Fiber Alignment Directs Cell Motility Over Chemotactic Gradients" Biotechnology and Bioengineering, 110, 1249-1254, 2013 (Year: 2013).*

Ziv, Polat, "The Role of Neurotrophic Factors Conjugated to Iron Oxide Nanoparticles in Peripheral Nerve Regeneration: In Vitro Studies" BioMed Research International, 2014, 2014 (Year: 2014).*

International Search Report in International Application No. PCT/US2015/052639, filed Sep. 28, 2015.

Bouta et al., Biomaterial guides for lymphatic endothelial cell alignment and migration, *Acta* Biomaterialia 7, www.elsevier.com/locate/actabiomat, 2010, pp. 1104-1113, Elsevier Ltd.

Wang et al., Biomimetic electrospun nanofibrous structures for tissue engineering, Materials Today, Jun. 6, 2013, pp. 229-241, vol. 16, Elsevier Ltd.

Xie et al., Electrospun nanofibers for neural tissue engineering, Nanoscale, www.rsc.org/nanoscale, 2010, pp. 35-43, The Royal Society of Chemistry 2010.

European Search Report, European Patent Application No. 15843768.1, dated Feb. 16, 2018.

* cited by examiner

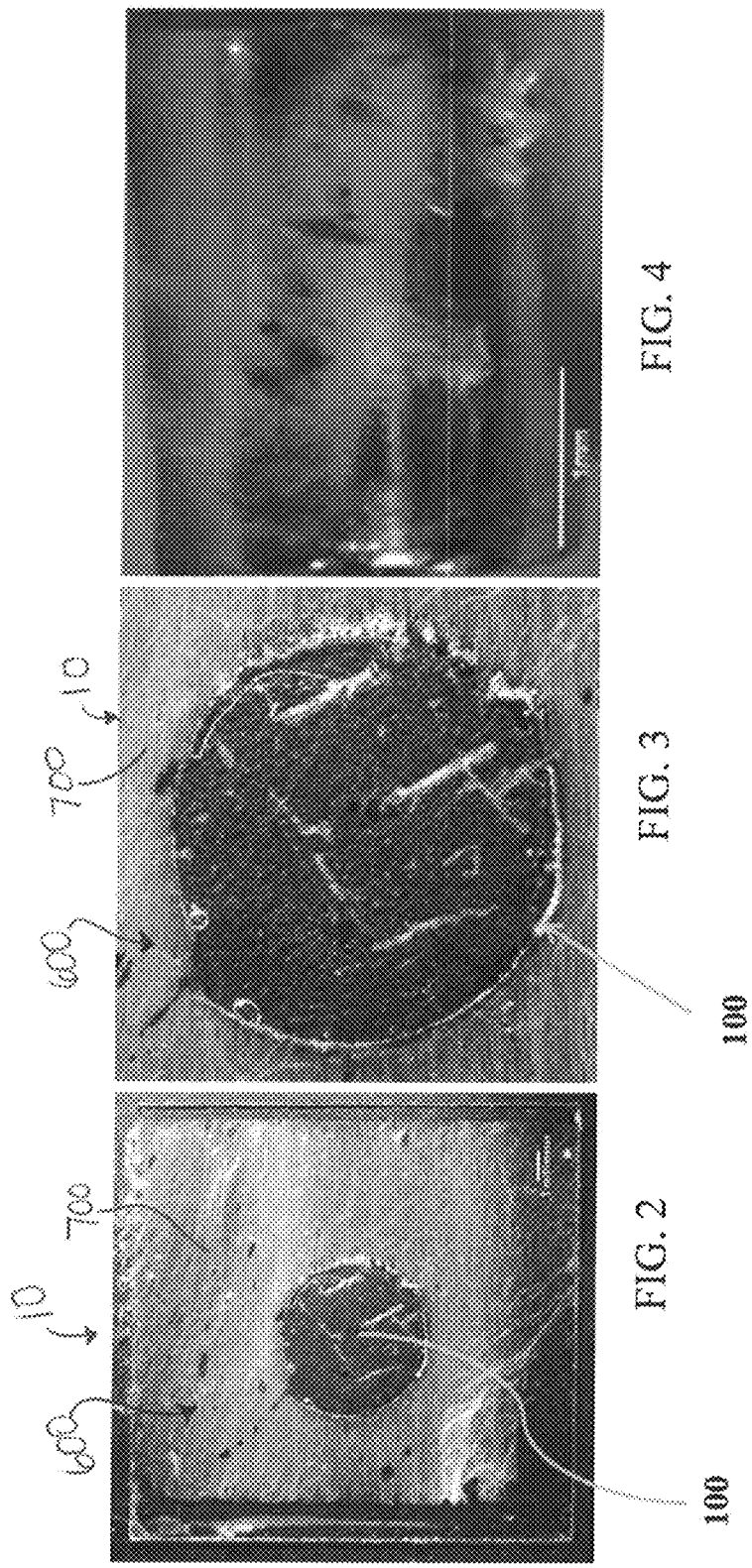

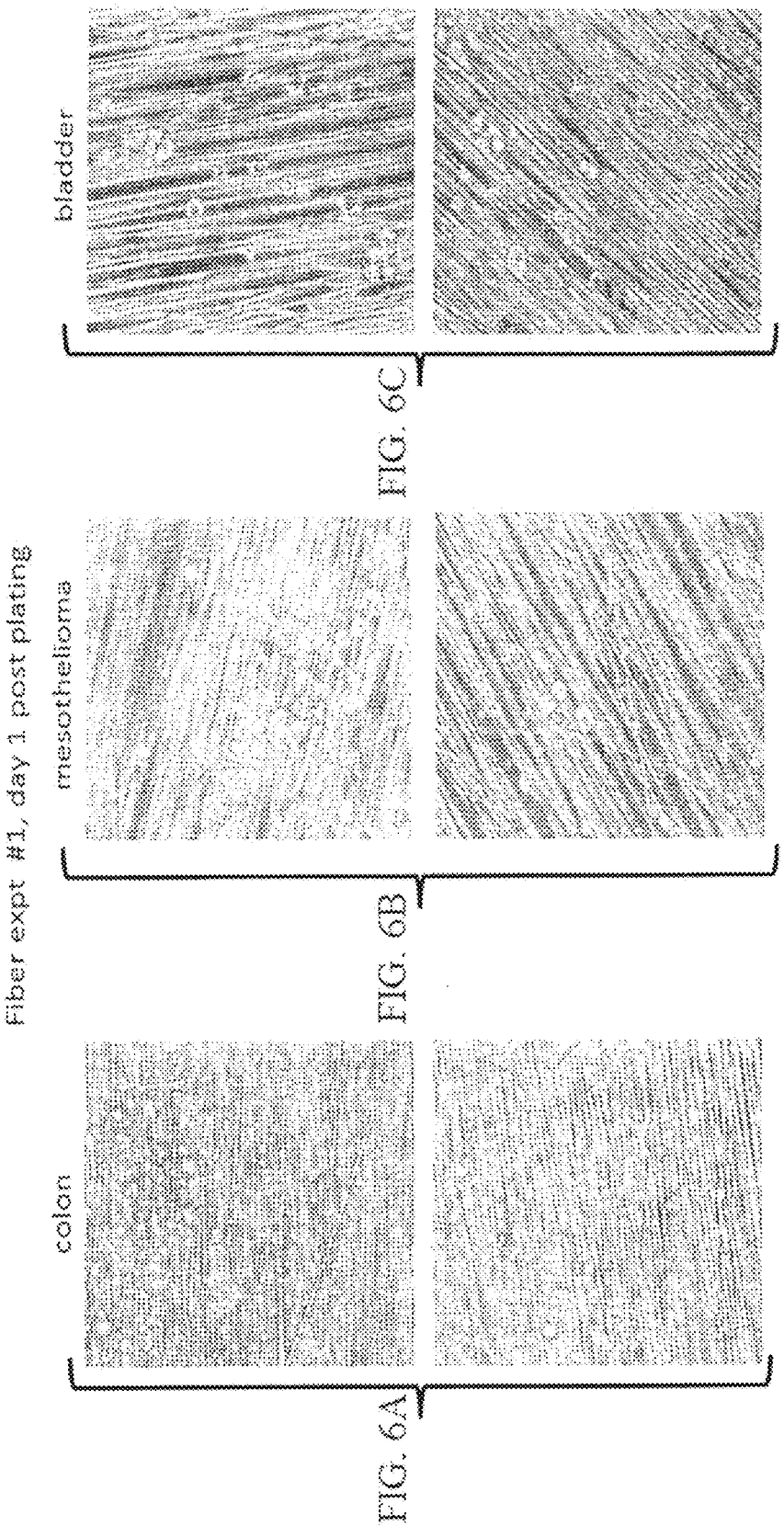

NANOCOMPOSITE SCAFFOLD FOR THE IN VITRO ISOLATION OF CELLS

CROSS-REFERENCE TO A RELATED APPLICATION

This application is the U.S. national stage application of international Patent Application No. PCT/US2015/052639, filed Sep. 28, 2015, which claims the benefit of U.S. Provisional Application Ser. No. 62/056,013, filed Sep. 26, 2014, which are incorporated herein by reference in their entirety.

GOVERNMENT SUPPORT

The subject invention was made with government support under a research project supported by the National Science Foundation grant number IIP-1358895. The government has certain rights in the invention.

BACKGROUND OF THE INVENTION

Current chemotherapy strategies struggle to deal with the variability of cancer. Given the variations in the disease from patient to patient, individual, patient-specific treatments would likely be more successful than current methods. In order to create these individualized treatments, the cancer cells from each patient must be isolated and analyzed. Previous methods of cancer cell isolation from tumor samples are insufficient. These methods do not isolate cancer cells with enough specificity, and typically rely on techniques likely to alter the cancer cells; these alterations may in turn disrupt the analysis necessary for prescription of individualized treatment. In order to allow for cancer cell analysis, isolation strategies must isolate purely cancerous cells from tumor biopsies while preserving the physical and biochemical characteristics of the cells.

BRIEF SUMMARY OF THE INVENTION

The present invention provides a cell culture apparatus (i.e., scaffold) for cell-type specific separation (e.g., the separation of cancer cells and/or normal cells) from a mixed population of cells, comprising a substrate comprising a surface of aligned fibers; one or more areas of the substrate comprising a protein layer in contact with the aligned fibers; and one or more chemoattractants disposed on at least one of the one or more areas of the substrate.

In some embodiments, the apparatus can include a void region having no layer of fibers on the substrate. Alternatively, the void region may have a layer of fibers with no protein layer. In one embodiment, the void region can serve as an area to place a tumor or population of cells for cell specific separation.

In some embodiments, the aligned fibers comprise poly L-lactide (PLLA).

In some embodiments, the protein layer comprises a protein that encourages cancer cell migration. In one embodiment, the protein further discourages fibroblast migration. In one embodiment, the protein that encourages cancer cell migration comprises laminin. In alternative embodiments, the protein layer comprises a protein that encourages fibroblast migration. In one embodiment, a protein that encourages fibroblast migration comprises collagen.

In some embodiments, the one or more chemoattractants are cancer cell chemoattractants. In other embodiments, the one or more chemoattractants are fibroblast chemoattractants. In one embodiment, the one or more chemoattractants are releasably contained in one or more nanospheres. In another embodiment, the nanospheres are magnetic, whereby the nanospheres can be held in position on the substrate magnetically.

In another aspect, the apparatus of the present invention comprises an additional area of the substrate comprising a protein layer that either encourages or discourages fibroblast migration in contact with the aligned fibers. In one embodiment, the protein layer of the additional area encourages fibroblast migration (and discourages cancer cell migration) (e.g., the protein layer comprises collagen). In another embodiment, the protein layer of the additional area discourages fibroblast migration (and encourages cancer cell migration) (e.g., the protein layer comprises laminin) For example, in one embodiment, the apparatus of the present invention comprises a substrate comprising a surface of aligned fibers; an area of the substrate comprising a protein layer in contact with the aligned fibers which encourages fibroblast migration; an additional area of the substrate comprising a protein layer in contact with the aligned fibers that encourages cancer cell migration; and one or more chemoattractants disposed on at least one of the one or more areas of the substrate.

In a further embodiment, the apparatus of the present invention comprises a substrate comprising a surface of aligned fibers; an area of the substrate comprising a protein layer in contact with the aligned fibers which encourages fibroblast migration; an additional area of the substrate comprising a protein layer in contact with the aligned fibers that encourages cancer cell migration; one or more chemoattractants that attract fibroblasts disposed on the area of the substrate comprising a protein layer that encourages fibroblast migration; and one or more chemoattractants that attract cancer cells disposed on the additional area of the substrate comprising a protein layer that encourages cancer cell migration.

In another aspect, the present invention provides methods of sorting cells, comprising:

providing a substrate comprising a surface of aligned fibers, one or more areas of the substrate comprising a protein layer in contact with the aligned fibers, and one or more chemoattractants disposed on at least one of the one or more areas of the substrate; and contacting the substrate with a mixed population of cells, whereby the one or more chemoattractants attract a specific population of cells from the mixed population such that the specific population migrates toward the chemoattractants. In some embodiments of the methods described, the protein layer on one or more areas of the substrate is selected from laminin, collagen, and a combination thereof. In some embodiments, the apparatus utilized in the methods described comprises an area of the substrate comprising a protein layer in contact with the aligned fibers that encourages fibroblast migration and an additional area of the substrate comprising a protein layer in contact with the aligned fibers that encourages cancer cell migration, whereby cancer cells and fibroblast cells are sorted from the mixed population. In some embodiments, the mixed population of cells is in a tumor.

In another aspect, the present invention provides kits for sorting cells from a mixed population of cell-types. The kits of the present invention may include an apparatus of the present invention as described herein in combination with one or more reagents.

The apparatus, methods, and kits herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures.

FIG. 2 shows a device of an embodiment of the present invention, including a void space centrally located on the substrate.

FIG. 3 shows a close-up view of the void space shown in FIG. 2.

FIG. 4 shows poly-L-lactic acid nanospheres containing growth factor and iron oxide nanoparticles. The inclusion of iron oxide nanoparticles (brown) enables the mobility of the particles to distinct locations for directed migration of cells.

FIG. 6 shows images of (A) colon cancer cells, (B) mesothelioma cells, and (C) bladder cancer cells at day 1 post plating on scaffolds of the present invention.

DETAILED DESCRIPTION OF THE INVENTION

Figure 1:
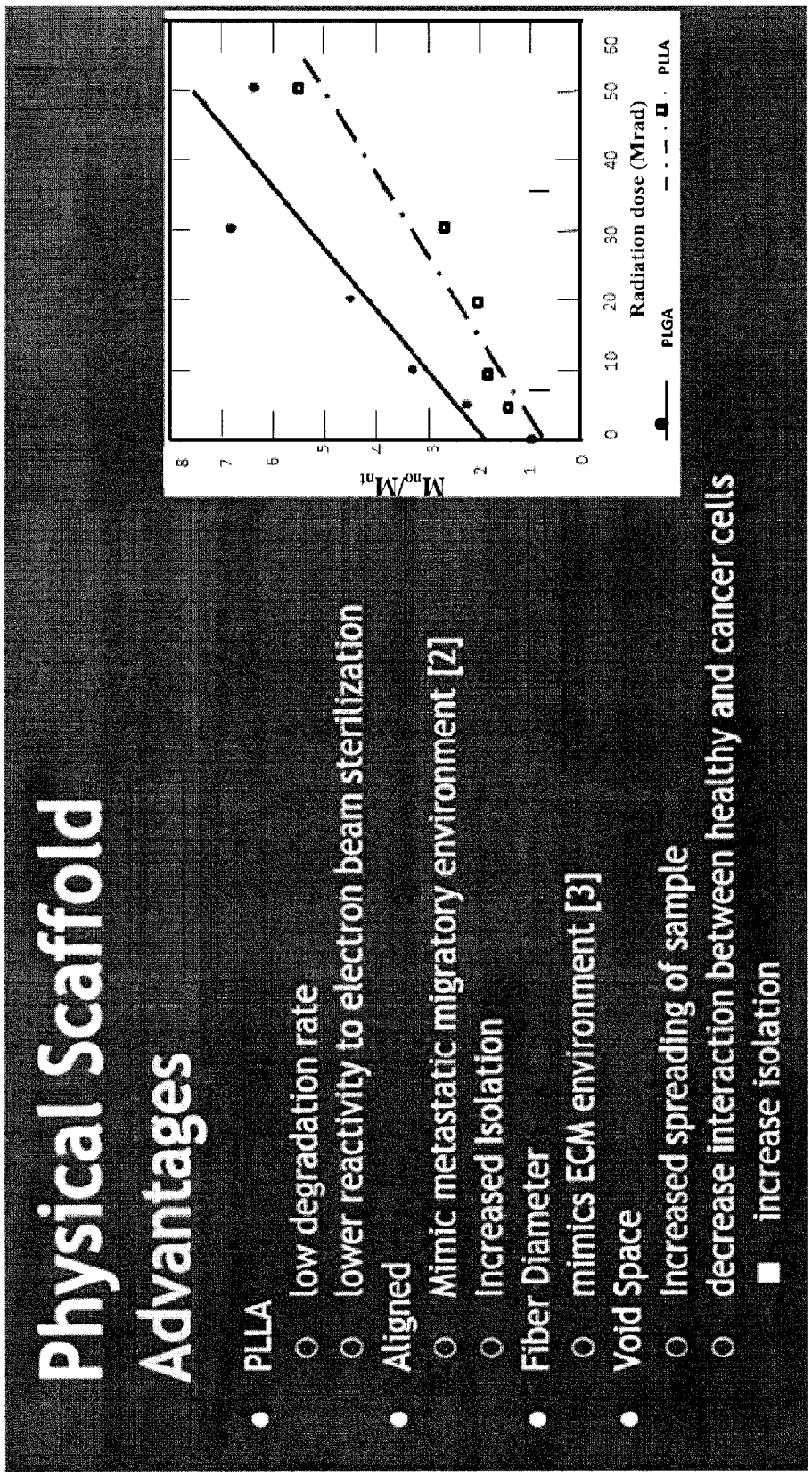
FIG. 1 shows some of the advantages of PLLA aligned fibers, including a graph.

The present invention is directed to devices, methods, and kits for cell-specific sorting of cells from a mixed population, e.g., from a tumor sample. Aspects of the present invention combine aligned electrospun microfibers with drug-releasing nanospheres to isolate cancer cells from tumor biopsies. Tumors are a mix of healthy cells and cancer cells. In order to study a specific cancer to determine the most effective therapy, cancerous cells from the tumor must be isolated and grown into a pure cell line, and, to this end, the present invention provides a means to specifically isolate cancer cells from a tumor.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines, and animals. The present invention is not limited by the illustrated ordering of acts or events, as some acts may occur in different orders and/or concurrently with other acts or events. Furthermore, not all illustrated acts, steps, or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

In one aspect, the present invention provides cell culture devices for cell-type specific separation (e.g., the separation of cancer cells and/or normal cells) from a mixed population of cells, comprising a substrate comprising a surface of aligned fibers; one or more areas of the substrate comprising a protein layer in contact with the aligned fibers; and one or more chemoattractants disposed on at least one of the one or more areas of the substrate.

The apparatus can also include a void region having no layer of fibers on the substrate. Alternatively, the void region may have a layer of fibers with no protein layer. This void region can serve as an area to place a tumor or a mixed population of cells for cell specific separation to begin. The void region increases the spreading of the tumor sample and helps to decrease the interaction between healthy and cancerous cells. A device of the present invention is shown with a void region 100 in FIG. 2 and FIG. 3.

In some embodiments, the aligned fibers comprise poly L-lactide (PLLA). In some embodiments, the aligned fibers are electrospun fibers that are extruded onto the substrate. The layer of aligned, electrospun fibers imitates the extracellular matrix surrounding tumor cells. Electrospun fibers are tiny strands of polymer that are extruded onto a substrate (e.g., a glass slide). Once a tumor biopsy or population of cells is deposited onto this fiber layer, cells are prompted to migrate by the presence of the fibers. The fibers are aligned, which promotes directional migration of cells by providing topographical cues. Cancer cells survive about 75% of the time on fibers alone, compared with a 25% survival rate for current methods. Some of the advantages of PLLA and aligned fibers are summarized in FIG. 1.

In some embodiments of the present invention, the protein layer on the surface of the substrate can include either proteins that encourage cancer cell migration or proteins that encourage healthy cell migration (e.g., fibroblast cells). Laminin and collagen are proteins found in the body and can be utilized in the protein layers of the device described herein. Cancer cells grow on laminin, but healthy cells do not. Further, collagen has been shown to promote migration of healthy (non-cancerous) cells, such as fibroblasts. In some embodiments of the present invention, the protein layer comprises a protein that encourages cancer cell migration, such as laminin. In one embodiment, the protein further discourages fibroblast migration. In alternative embodiments, the protein layer comprises a protein that encourages fibroblast migration, such as collagen.

In some embodiments, chemoattractants are utilized with the devices and methods of the present invention to increase the separation of cell types. Chemoattractants are chemicals or proteins released by various cells in the body that signal other cells to migrate to the location of the chemoattractants. Many cancer cells have commonly overexpressed receptors for certain chemoattractants, which help them migrate to new parts of a subject's body. In some embodiments, one or more chemoattractants are cancer cell chemoattractants. Common growth factors (i.e., chemoattractants) that have been shown to induce cancer migration are EGF, VEGF, ILGF-1, and HGF [1-3]. Overexpressed cell surface receptors such as CXCR4 and EpCAM have similarly been involved in chemotactic migration and cell attachment [4]. Because many cell adhesion factors are responsible for the expression of factors such as ILGF-1, HGF, and the ligand binding CXCR4 [2,4], directing migration of fibroblasts away from the tumor mass is possible. For example, EGF, VEGF, ILGF-1, and/or HGF may be utilized as chemoattractants for breast cancer cells; VEGF, ILGF-1, and/or CXCL-12 may be utilized as chemoattractants for pancreatic cancer cells; VEGF may be utilized as a chemoattractant for brain cancer cells; EGF, VEGF, and/or HGF may be utilized as chemoattractants for lung cancer cells; and ILGF-1 may be utilized as a chemoattractant for melanoma cells. As would be understood by those skilled in the art, any factor known in the art to act as a chemoattractant for one or more type of cancer cells may be utilized in the devices, kits, and methods of the present invention. Furthermore, the devices of the present invention may be utilized as a kit or tool to screen for novel cancer cell chemoattractants.

In other embodiments, one or more of the chemoattractants are fibroblast chemoattractants. Commonly known signaling molecules which enhance fibroblast movements and may be used for this purpose are platelet derived growth factor (PDGF) and collagen. Conversely, substances such as tissue factor pathway inhibitor-2 (TFPI-2) and fibroblast activation protein (FAP) pro-toxin limit fibroblast growth and migration [5]. For example, IL-4 may be utilized as a chemoattractant for fibroblasts, and TFPI-2 and/or FAP may be utilized to hinder fibroblast migration. As would be understood by those skilled in the art, any factor known in the art to act as a chemoattractant for one or more type of normal cells or fibroblasts may be utilized in the devices and methods of the present invention.

In another aspect, the apparatus of the present invention comprises an additional area of the substrate comprising a protein layer. The additional area can include a protein layer that either encourages normal cell (e.g., fibroblast) migration or, alternatively, encourages cancer cell migration in contact with the aligned fibers. In one embodiment, the protein layer of the additional area encourages fibroblast migration (and discourages cancer cell migration) (e.g., the protein layer comprises collagen). In an alternative embodiment, the protein layer of the additional area discourages fibroblast migration (and encourages cancer cell migration) (e.g., the protein layer comprises laminin) For example, in one embodiment, the apparatus of the present invention comprises a substrate comprising a surface of aligned fibers; an area of the substrate comprising a protein layer in contact with the aligned fibers which encourages fibroblast migration; an additional area of the substrate comprising a protein layer in contact with the aligned fibers that encourages cancer cell migration; and one or more chemoattractants disposed on at least one of the one or more areas of the substrate.

Figure 5:
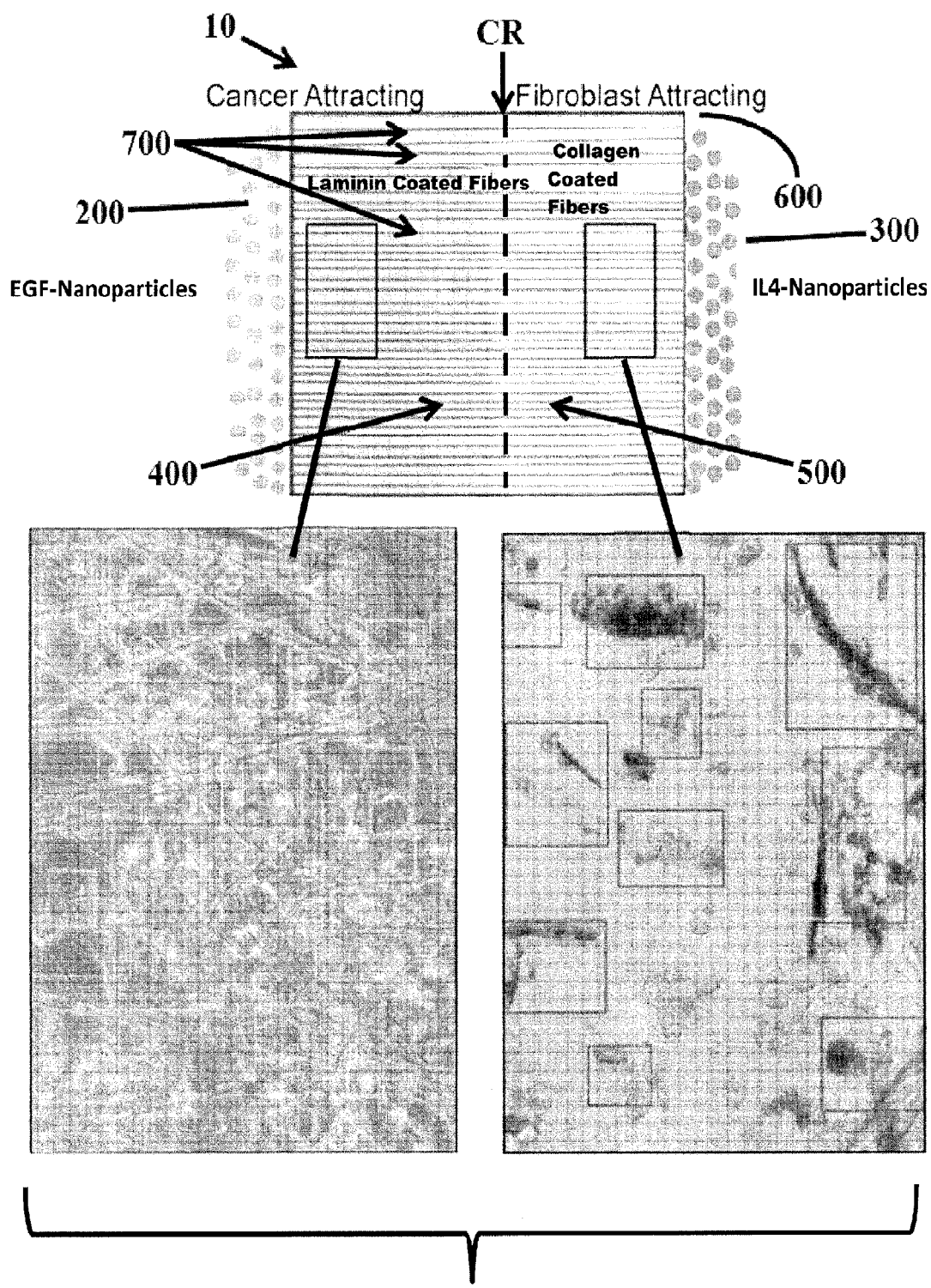
FIG. 5 shows a device of an embodiment of the present invention, including two separate protein layers located on the substrate. The figure also shows enlarged views of the protein layer on each side of the device.
Figures 7A, 7B, 7C:
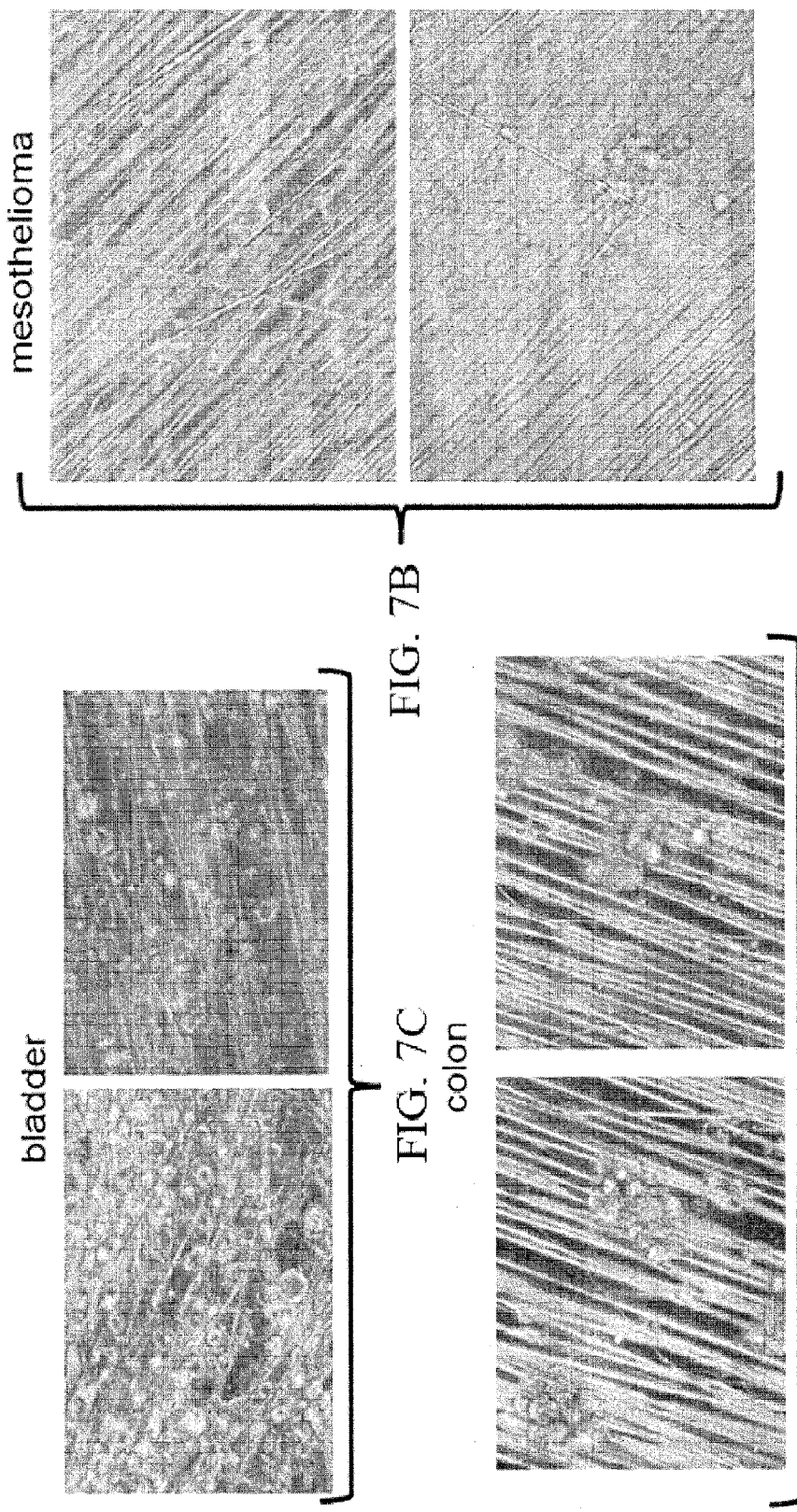
FIG. 7 shows images of (A) colon cancer cells, (B) mesothelioma cells, and (C) bladder cancer cells at day 7 post plating showing migration of the cells on scaffolds of the present invention.

In a further embodiment, the apparatus of the present invention comprises a substrate comprising a surface of aligned fibers; an area of the substrate comprising a protein layer in contact with the aligned fibers which encourages fibroblast migration; an additional area of the substrate comprising a protein layer in contact with the aligned fibers that encourages cancer cell migration; one or more chemoattractants that attract fibroblasts disposed on the area of the substrate comprising a protein layer that encourages fibroblast migration; and one or more chemoattractants that attract cancer cells disposed on the additional area of the substrate comprising a protein layer that encourages cancer cell migration. This embodiment provides a device that can be utilized to separate cancer cells and fibroblasts from a mixed population of cells (e.g., a tumor sample) that is placed on the device. For example, and as illustrated in FIG. 5, half of the substrate may be coated in laminin, while the other half is coated in collagen. Since laminin has been shown previously to discourage fibroblast migration while allowing robust migration of cancer cells and collagen has been shown to prompt fibroblast adhesion and migration, the protein coating assists in the separation of cancer cells and healthy fibroblasts from the tumor biopsy. As these two cell types are strongly symbiotic, separation of the two is difficult and has not been consistently achieved with existing technology.

In one embodiment, the one or more chemoattractants are releasably contained in one or more nanospheres. Nanospheres are tiny polymer beads, which may contain an iron oxide core. The polymer can hold chemoattractants inside it, which are released from the nanospheres as the polymer degrades and create a gradient for cells to migrate towards along the substrate. For example, and as illustrated in FIG. 5, the chemoattractant filled nanospheres 200, 300 may be placed into trenches on either side of a central region CR separating the laminin 400 and collagen 500 protein layers on the fiber 700 covered substrate 600 of the device 10. The pool of the mixed population of cells and/or tumor sample(s) is placed along the central region CR for separation to one side or the other of the substrate, based on the cell-types being separated/isolated.

In another embodiment, the nanospheres are magnetic, whereby the nanospheres can be held in position on the substrate magnetically versus utilizing a trenched area. This portion consists of drug-releasing magnetic nanospheres that are loaded via physical entrapment of a drug or protein within a polymer shell. As such, these nanospheres can be loaded with a range of different drugs, as illustrated, for example, in FIG. 5 for EGF-nanoparticles and IL-4-nanoparticles. In the use of this embodiment of the invention for cancer cell isolation, one set of nanospheres contains chemoattractants for cancer cells, while a second contains attractants for healthy cells. These two sets are placed on opposite ends of the scaffold and held in place magnetically. As they release their drugs, they direct cancer cells and healthy cells to migrate in opposite directions.

The combination of fibers, protein coating, and chemoattractant delivery inherent in this invention is unique. Such a combination has not been combined previously in an effort to create in vitro cell isolation.

In another aspect, the present invention provides methods of sorting cells, comprising:

providing a substrate comprising a surface of aligned fibers, one or more areas of the substrate comprising a protein layer in contact with the aligned fibers, and one or more chemoattractants disposed on at least one of the one or more areas of the substrate; and contacting the substrate with a mixed population of cells, whereby the one or more chemoattractants attract a specific population of cells from the mixed population such that the specific population migrates toward the chemoattractants.

In some embodiments of the methods described, the one or more areas of the substrate comprising a protein layer include proteins selected from laminin, collagen, and a combination thereof. In some embodiments, the apparatus comprises an area of the substrate comprising a protein layer in contact with the aligned fibers which encourages fibroblast migration and an additional area of the substrate comprising a protein layer in contact with the aligned fibers that encourages cancer cell migration, whereby cancer cells and fibroblast cells are sorted from the mixed population. In some embodiments, the mixed population of cells is in a tumor.

In another aspect, the present invention provides kits for sorting cells from a mixed population of cell-types. The kits of the present invention may include an apparatus of the present invention as described herein in combination with one or more reagents. The kits may further be used in the methods described herein. The kits may also include at least one reagent and/or instructions for their use. Also, the kits may include one or more containers filled with reagent(s). Furthermore, the kits may include additional components for harvesting and culturing cells from the devices of the present invention.

In certain embodiments, the kits may additionally include reagents and means for detecting cancer cell markers and/or healthy cell (e.g., fibroblast) markers. The means of allowing detection may be by conjugation of detectable labels or substrates, such as fluorescent compounds, enzymes, radioisotopes, heavy atoms, reporter genes, luminescent compounds, or additional antibodies. As it would be understood by those skilled in the art, additional detection or labeling methodologies may be used in the kits provided. Detection of cancer cell markers and/or healthy cell markers may be utilized to confirm proper isolation of the target cell type(s).

Examples

The methods and devices herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

Cell Isolation Device—

The device comprises a substrate with a surface of aligned, electrospun fibers with one area containing a laminin protein layer and another area containing a collagen protein layer; and chemoattractant nanoparticles on opposing ends of the substrate.

Cancer Cell Isolation and Culture—

1. Inoculation—A tumor is placed onto the void space site on the substrate.

2. Growth—Healthy cells and cancer cells grow onto the fibers. Aligned fibers allow cells to migrate.

3. Separation—Nanospheres containing factors attract the different cells types to opposite ends. The nanospheres release factors to create a gradient that induces cell migration.

4. Migration—As the nanospheres degrade and release the growth factors inside them, cells migrate along the fibers. One side has factors that only attract cancer cells; the other side has factors that only attract healthy cells.

5. Proliferation—The cells are encouraged to grow on the scaffold by their favorite growth factors. An invisible protein coating on one side discourages healthy cells from growing onto the cancer cell side.

6. Harvesting—After the cells have grown on both sides of the scaffold, cancer cells are harvested for further research.

7. Analysis—Cancer cells from the scaffold are tested for purity and cultured into a cancer cell line. This cell line can then be used to prescribe the best treatment method for the specific tumor. Personalized cancer treatment therapies can be prescribed based on the genomic findings.

Examples of Cancer Cell Isolation—

FIGS. 6A, 6B, and 6C and FIGS. 7A, 7B, and 7C show images of colon cancer cells, mesothelioma cells, and bladder cancer cells at day 1 post plating and day 7 post plating, respectively, migrating on scaffolds of the present invention.

Discussion

Current technologies for the isolation of patient-specific cancer cells lack specificity, reliability, and are time- and cost-intensive. The invention described herein circumvents these limitations by mimicking the tumor microenvironment found in vivo. By providing cancer cells with a novel combination of micro-topographical and biochemical cues, robust and reliable separation of cancerous and healthy cells can be achieved from biopsied tumor tissue. This separation occurs quickly and is non-reliant on human interaction. Instead, separation is achieved by replicating naturally found cues for cell migration, causing cancer cells to move away from healthy cells in the biopsied tissue. By mimicking the tumor microenvironment, rather than using synthetic chemicals or intense centrifugation to induce cell isolation, the cancer cells will retain their original physical and biochemical properties; this will allow researchers to analyze cancer cell behavior with unprecedented ease and accuracy. The present invention allows for more reliable, useful, and efficient analysis of patient-specific cancer cells than is possible given current technology.

The present invention has several advantages over existing technology. First of all, it is designed for more specific isolation of cancer cells than is possible with existing solutions. Protein coatings and chemoattractant delivery combine two methods for separating cancerous cells from healthy cells in a tumor biopsy; this combination leads to a more robust isolation than what is possible with current methods. In addition, the protein coating layer specifically deconstructs the relationship between cancer cells and healthy fibroblasts, allowing separation of the two cell types which is not possible with current technology. Current technologies typically rely on high-velocity centrifugation or treatment with synthetic chemicals in order to isolate cancer cells; these methods alter the physical and chemical properties of the cancer cells and increase the difficulty of accurately analyzing these cells for potential treatment. However, the invention uses natural, biomimetic cues in order to induce isolation. By using fibers, proteins, and chemoattractants that are found naturally in the tumor microenvironment, the invention will induce cell isolation while causing minimal alterations to the cancer cells. This will preserve cancer cell properties more than is possible with current technology, leading to increased ease of cell analysis.

Cancer cells found in the brain exhibit markedly different characteristics than those found in the liver or skin. As such, it is difficult to find chemoattractants which actively prompt migration in many different types of cancer cells. However, aspects of the present invention use nanospheres which can be loaded with a wide range of chemicals. As such, different chemoattractants can be loaded into the nanospheres in order to specifically target certain cancers and overcome the variability of cancer types.

Typically, the protein coating layer is designed to break the relationship between cancer cells and healthy fibroblasts, interdependent cells found in many tumors, it may not be sufficient to completely separate the cell types. However, by altering the release from the nanospheres or placing additional proteins within the coating layer, complete separation can be achieved even if the proposed coating layer is insufficient.

Although the primary application of this invention is for the isolation of cancer cells from biopsied tissues, there are many additional uses. Given the range of chemicals which can be loaded into the magnetic nanospheres, this invention could be used to isolate many different cell types from mixed-cell cultures. This isolation is useful for many different in vitro diagnostic and cell analysis purposes. For one example, individual islet cells can be isolated from pancreatic biopsies in order to examine their response to treatments for diabetes.

It is to be appreciated that the foregoing Detailed Description section, and not the Abstract section, is intended to be used to interpret the claims. The Abstract section may set forth one or more, but not all, exemplary embodiments of the present invention as contemplated by the inventor(s), and thus, is not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

REFERENCES 1. http://www.who.int/mediacentre/factsheets/fs297/en/accessed Feb. 8, 2014.
2. http://www.cdc.gov/nchs/fastats/lcod.htm accessed Feb. 8, 2014
3. Burrner, R. A Genomics-Based Classification of Human Lung Tumors. Sci Transl Med. 5:209. 2013.
4. http://www.cancer.org/acs/groups/contet/@research/document/acspc-041770.pdfaccessed Feb. 8, 2014
5. Räsänen K, Vaheri A. Activation of fibroblasts in cancer stroma. Experimental Cell Research, 2010; 316:2713-2722.

The invention claimed is:

1. A cell culture apparatus for cell-type specific separation of a mixed population of cells, comprising:
    a substrate comprising a surface of aligned fibers;
    one or more areas of the substrate comprising a protein layer in contact with the aligned fibers, wherein a first area includes a first protein layer including a first protein that encourages cancer cell migration, and wherein a second area includes a second protein layer including a second protein that encourages fibroblast migration; and
    one or more chemoattractants disposed on at least one of the one or more areas of the substrate.

2. The apparatus of claim 1, wherein the substrate further comprises a void region-, the void region having no layer of fibers on the substrate.

3. The apparatus of claim 1, wherein the aligned fibers comprise poly L-lactide (PLLA).

4. The apparatus of claim 1, wherein the first protein layer discourages fibroblast migration.

5. The apparatus of claim 1, wherein the first protein layer includes laminin.

6. The apparatus of claim 1, wherein the one or more chemoattractants are cancer cell chemoattractants.

7. The apparatus of claim 1, wherein the one or more chemoattractants are releasably contained in one or more nanospheres.

8. The apparatus of claim 7, wherein the nanospheres are magnetic, whereby the nanospheres can be held in position on the substrate magnetically.

9. The apparatus of claim 1, wherein the one or more chemoattractants are fibroblast chemoattractants.

10. The apparatus of claim 9, wherein the one or more chemoattractants are releasably contained in one or more nanospheres.

11. The apparatus of claim 10, wherein the nanospheres are magnetic, whereby the nanospheres can be held in position on the substrate magnetically.

12. The apparatus of claim 1, wherein the second protein layer that includes collagen.

13. A method of sorting cells, comprising:
    providing a substrate comprising a surface of aligned fibers, one or more areas of the substrate comprising a protein layer in contact with the aligned fibers, and one or more chemoattractants disposed on at least one of the one or more areas of the substrate, wherein a first area includes a first protein layer including a first protein that encourages cancer cell migration, and wherein a second area includes a second protein layer including a second protein that encourages fibroblast migration; and
    contacting the substrate with a mixed population of cells, whereby the one or more chemoattractants attract a specific population of cells from the mixed population such that the specific population migrates toward the chemoattractants.

14. The method of claim 13, wherein the protein layer on one or more areas of the substrate is selected from laminin, collagen, and a combination thereof.

* * * * *